(12) United States Patent
Alshemari

(10) Patent No.: US 8,529,495 B1
(45) Date of Patent: Sep. 10, 2013

(54) MIDDLE EAR VENTILATION TUBE

(71) Applicant: Hasan M. Sh. Sh. Alshemari, Saad Al Abdulla (KW)

(72) Inventor: Hasan M. Sh. Sh. Alshemari, Saad Al Abdulla (KW)

( * ) Notice: Subject to any disclaimer, the term of this patent is extended or adjusted under 35 U.S.C. 154(b) by 0 days.

(21) Appl. No.: 13/633,779

(22) Filed: Oct. 2, 2012

(51) Int. Cl.
A61B 19/00 (2006.01)

(52) U.S. Cl.
USPC .............................. 604/8; 604/294

(58) Field of Classification Search
None
See application file for complete search history.

(56) References Cited

U.S. PATENT DOCUMENTS

| 3,807,409 | A | * | 4/1974 | Paparella et al. ............. 604/264 |
| 3,871,380 | A | | 3/1975 | Heros |
| 4,174,716 | A | | 11/1979 | Treace |
| 4,468,218 | A | | 8/1984 | Armstrong |
| 4,650,488 | A | | 3/1987 | Bays et al. |
| 4,695,275 | A | | 9/1987 | Bruce et al. |
| 5,139,502 | A | * | 8/1992 | Berg et al. ..................... 606/108 |
| 5,178,623 | A | | 1/1993 | Cinberg et al. |
| 5,807,303 | A | | 9/1998 | Bays |
| 7,097,661 | B2 | | 8/2006 | Perry |
| 2003/0187456 | A1 | * | 10/2003 | Perry ............................ 606/109 |

FOREIGN PATENT DOCUMENTS

GB 2316319 2/1998

* cited by examiner

Primary Examiner — Leslie Deak
Assistant Examiner — Sara Sass
(74) Attorney, Agent, or Firm — Richard C. Litman

(57) ABSTRACT

The middle ear ventilation tube is a ventilation tube for placement through an opening formed through the tympanic membrane to drain fluid from the middle ear to the ear canal or outer ear. The middle ear ventilation tube includes a hollow, substantially cylindrical tube having axially opposed first and second open ends. A first annular flange is formed about the first open end of the tube. The first annular flange defines a tapered angled edge for insertion through an opening formed through the patient's tympanic membrane. A second annular flange is formed about the second open end of the tube. The second annular flange has a tongue portion extending outwardly therefrom for grasping and manipulation. A notch is formed in the tongue portion, and a pair of recesses are formed in the second annular flange, each for engaging a needle for fine adjustment within the ear.

7 Claims, 6 Drawing Sheets

MIDDLE EAR VENTILATION TUBE

BACKGROUND OF THE INVENTION

1. Field of the Invention

The present invention relates to drainage and ventilation tubes for the middle ear, and particularly to a middle ear ventilation tube provided with an outer flange for adjustment and positioning.

2. Description of the Related Art

The installation of tubes in the tympanic membrane, which separates the middle ear from the outer ear, is a well-known remedy for treating inflammation of the middle ear, or otitis media. Typically, a myringotomy is performed to create an opening in the tympanic membrane, and a vent or drain in the form of a tube is inserted into the opening to permit drainage of fluid from the middle ear to alleviate a buildup or reduction of pressure in the middle ear cavity. The tube functions to maintain the opening in the tympanic membrane for a sufficient period of time following the surgery to allow pressure to equalize between the middle and outer ears. Frequently, the condition of buildup or reduction of pressure in the middle ear cavity, which the tube is intended to alleviate, requires that the tube remain in place for a significant period of time, ranging in duration from about six to about twenty-four months.

A variety of ventilation tubes for insertion into an opening in the tympanic membrane have been used over the years. Typical conventional ventilation tubes are generally cylindrical, allowing the cylindrical tubes to be inserted into the myringotomy opening. However, the procedure for forming the opening, insertion, and then adjustment of the ventilation tube is sometimes difficult, particularly due to the relatively small size of the ear canal. Incisions are often first made with a scalpel or similar instrument, and then the tube is inserted through the incision using forceps or the like. With respect to the size of the ear canal and the small incision formed through the tympanic membrane, the forceps are relatively large and bulky, thus decreasing the surgeon's line of sight with the ear, and making adjustments difficult.

Thus, a middle ear ventilation tube solving the aforementioned problems is desired.

SUMMARY OF THE INVENTION

The middle ear ventilation tube is a ventilation tube for placement through an opening formed through the tympanic membrane to drain fluid from the middle ear to the ear canal or outer ear. The middle ear ventilation tube includes a hollow, substantially cylindrical tube having axially opposed first and second open ends. A first annular flange is formed about the first open end of the tube. The first annular flange defines a tapered angled edge. A second annular flange is formed about the second open end of the tube. The second annular flange has a tongue portion extending outwardly therefrom. A notch is formed in an outer edge of the tongue portion, and a pair of recesses are formed in the second annular flange.

In use, the middle ear ventilation tube is inserted into the patient's ear canal. After conventionally forming an incision in the tympanic membrane, the tapered angled edge of the first annular flange is inserted through the opening formed through the tympanic membrane. The notch formed in the outer edge of the tongue portion is engaged with a straight tip needle to properly position the first annular flange adjacent the tympanic membrane within the patient's middle ear, and the second annular flange is positioned adjacent the tympanic membrane within the patient's ear canal. Additional fine manipulation and positioning is effected by engaging the pair of recesses with the tip of the straight tip needle.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
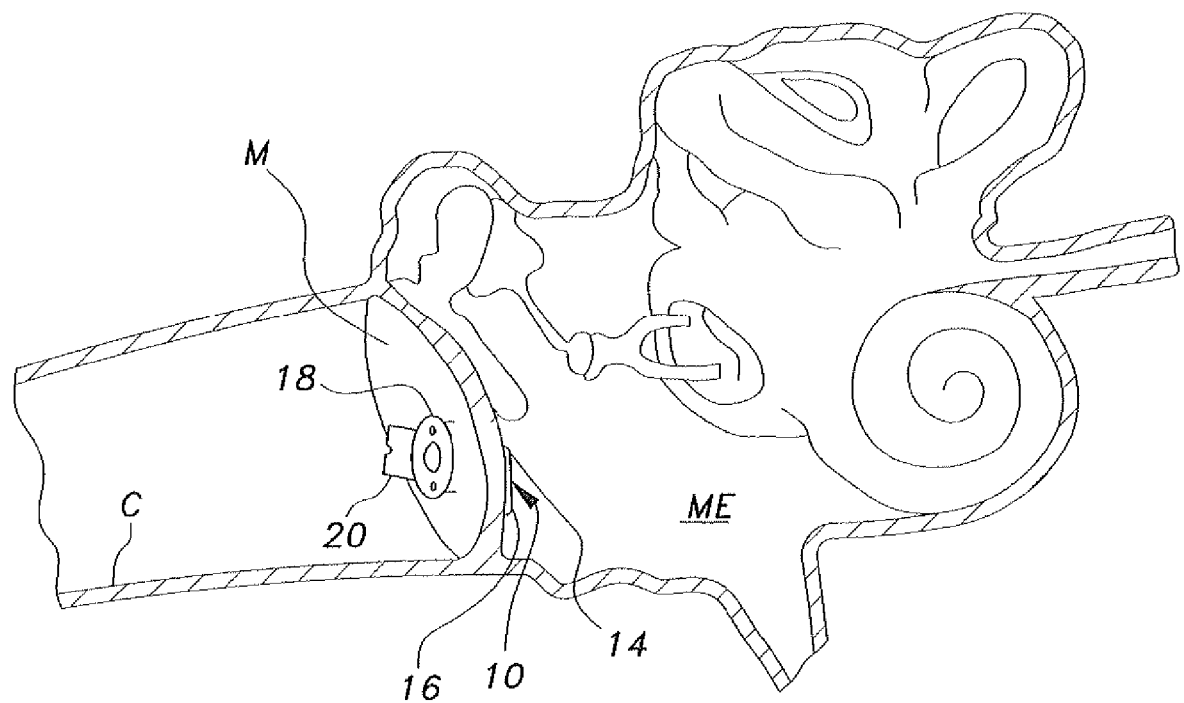
FIG. 1 is an environmental, perspective view of a middle ear ventilation tube according to the present invention, shown positioned to drain the middle ear.
Figure 2:
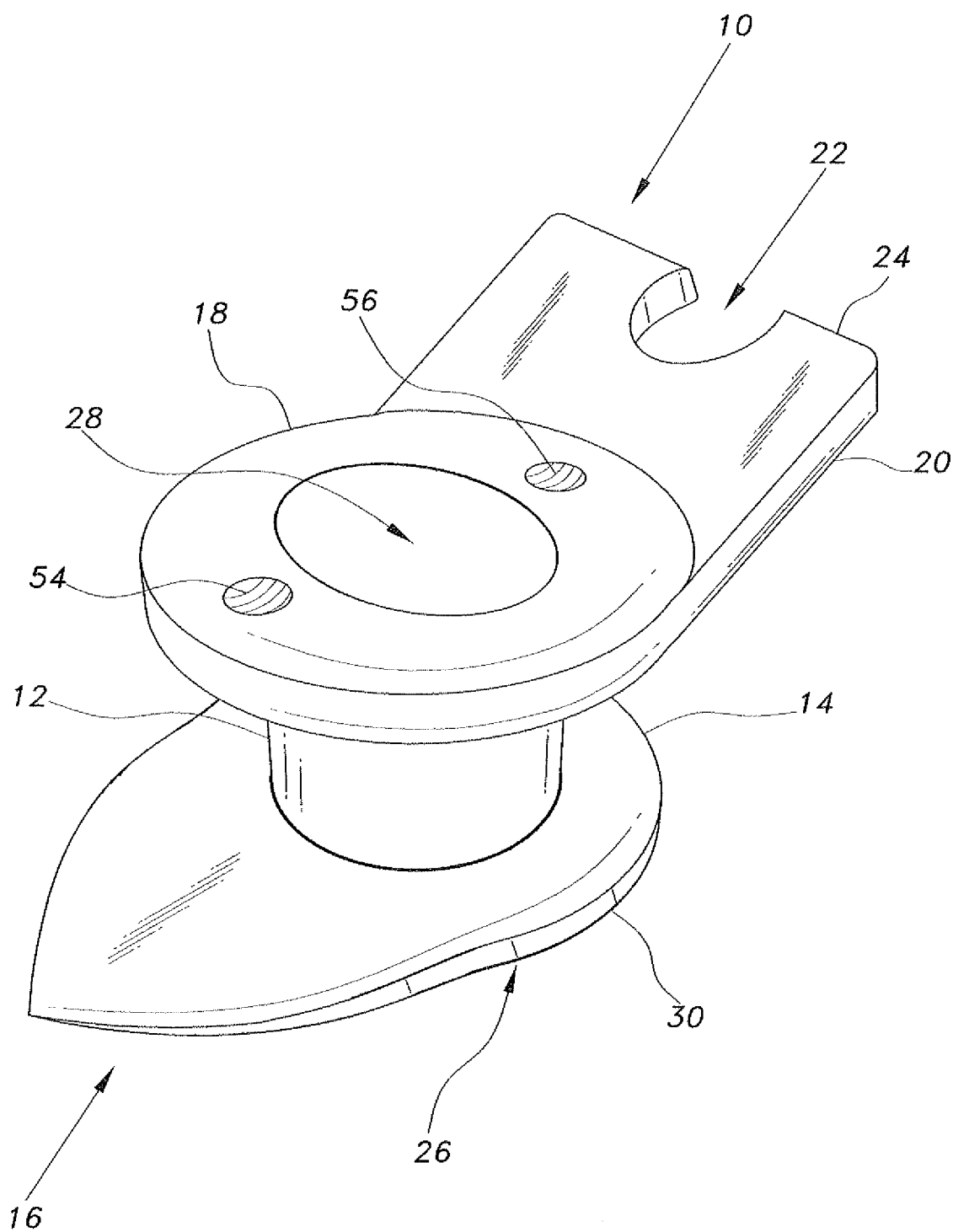
FIG. 2 is a perspective view of the middle ear ventilation tube according to the present invention.
Figure 3:
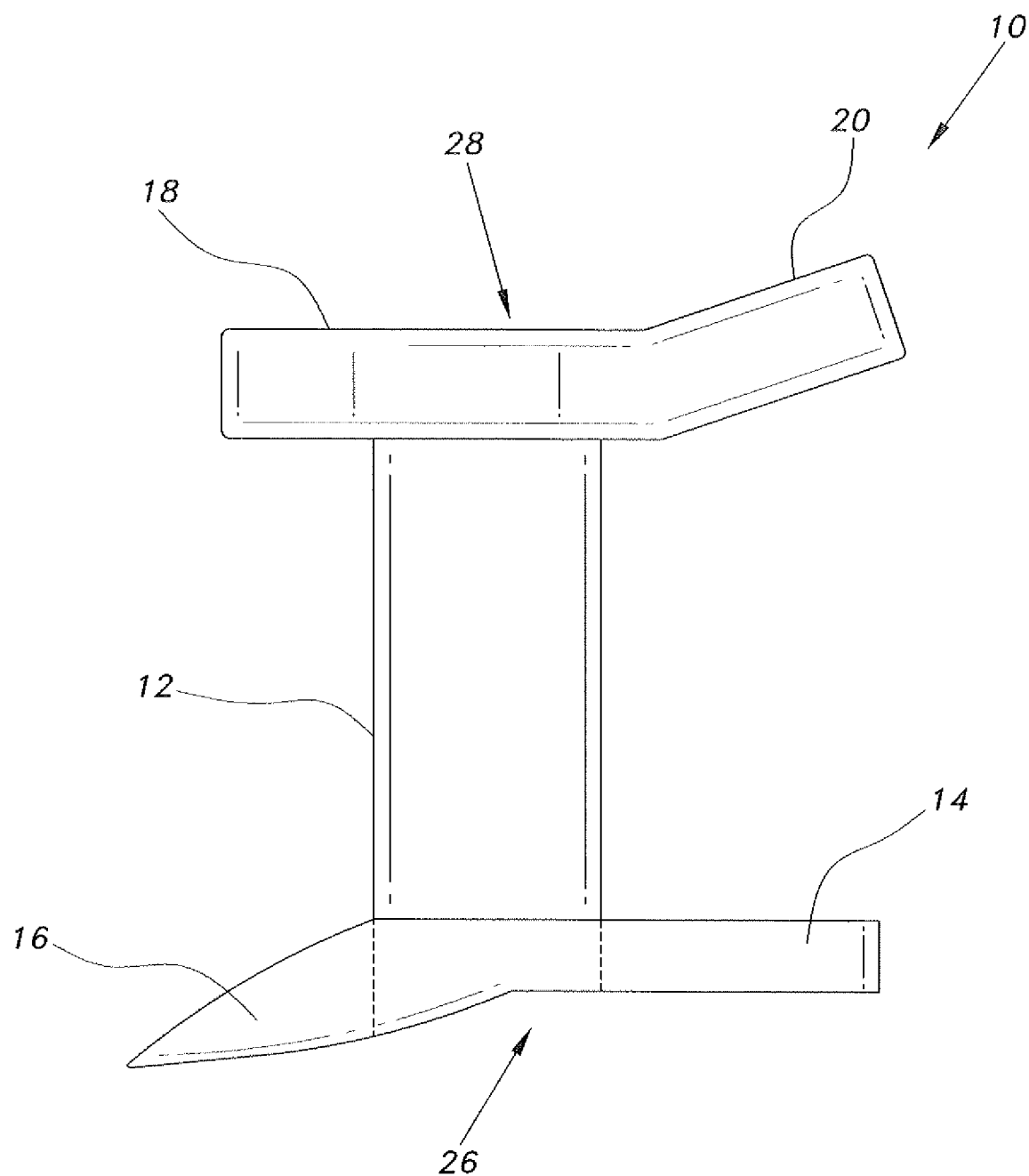
FIG. 3 is a side view of the middle ear ventilation tube of FIG. 2.

As shown in FIG. 1, the middle ear ventilation tube 10 is a ventilation tube for placement through an opening formed through the tympanic membrane M to drain fluid from the middle ear ME to the ear canal C or outer ear. As best seen in FIGS. 2 and 3, the middle ear ventilation tube 10 includes a hollow, substantially cylindrical tube 12 having axially opposed first and second open ends 26, 28, respectively. A first annular flange 14 is formed about the first open end 26 of the tube 12. The first annular flange 14 defines a tapered angled edge 16.

A second annular flange 18 is formed about the open second end 28 of the tube 12. The second annular flange 18 has a tongue portion 20 extending outwardly therefrom. A notch 22 is formed in an outer edge 24 of the tongue portion 20, and a pair of recesses 54, 56 are formed in the second annular flange 18. In FIG. 2, the pair of recesses 54, 56 are shown as being diametrically opposed and aligned along the axis of extension of both the tongue portion 20 and the tapered angled edge 16. It should be understood that any desired orientation or number of recesses may be used.

The first annular flange 14, the second annular flange 18, the tapered angled edge 16, the tongue portion 20 and the tube 12 may have any desired dimensions and configuration, the drawings being exemplary. The middle ear ventilation tube 10 may be formed from any suitable material that is biologically inert and compatible with human tissue. As with conventional ventilation tubes, the length of tube 12 may be varied, but is preferably substantially greater in length than the thickness of the tympanic membrane M.

As best seen in FIG. 2, the tapered angled edge 16 is preferably diametrically opposed from the tongue portion 20, allowing for ease of inserting the ventilation tube through an incision formed through membrane M when the tongue portion 20 is grasped, as will be described in detail below. The first annular flange 14 includes first and second portions. The first portion 30 defines an annular rim that extends outwardly from the tube along a direction substantially orthogonal to the axis of the tube 12 (i.e., in the radial direction from the tube 12). The second portion of the first annular flange 14 defines the tapered angled edge 16. The tapered angled edge 16 is preferably at an angle to the first portion 30. The tapered angled edge 16 preferably includes a pair of straight edges oriented at an acute angle with respect to one another, forming a substantially triangular shape, as shown. The tongue portion 20 is preferably similarly angled from the second annular flange 18. The tongue portion 20 and the tapered angled edge 16 preferably extend substantially parallel to one another, as best shown in FIG. 3.

Figure 4:
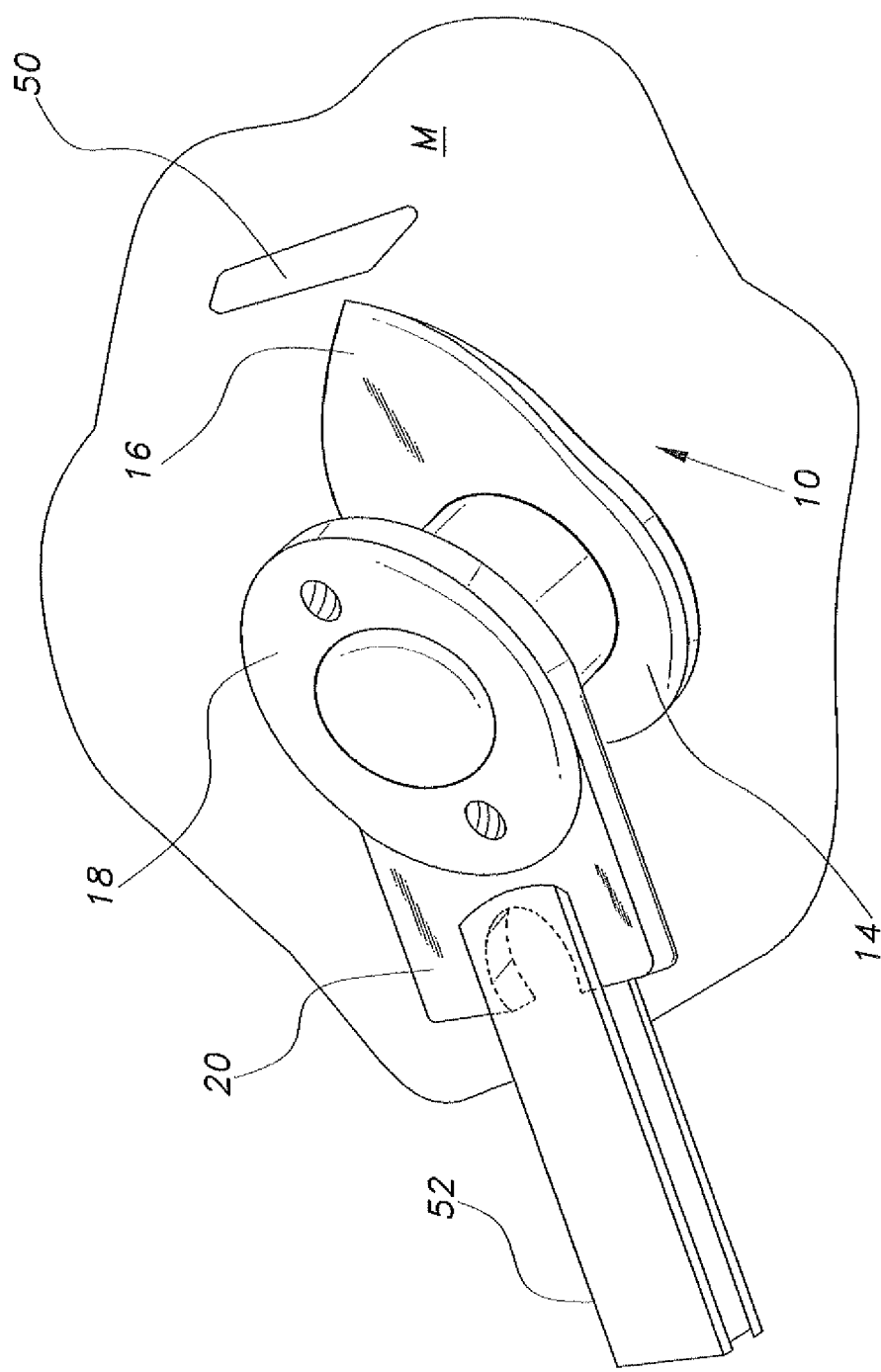
FIG. 4 is an environmental, perspective view of the middle ear ventilation tube of FIG. 2, illustrating initial insertion of the middle ear ventilation tube.

In use, as shown in FIG. 4, the middle ear ventilation tube 10 is inserted into the patient's ear canal. The tongue portion 20 is provided for grasping with forceps 52 or the like to position the tapered angled edge 16 adjacent the tympanic membrane M. The angling of the tongue portion 20 allows for easier manipulation of the tube 10 within the ear canal.

Figure 5:
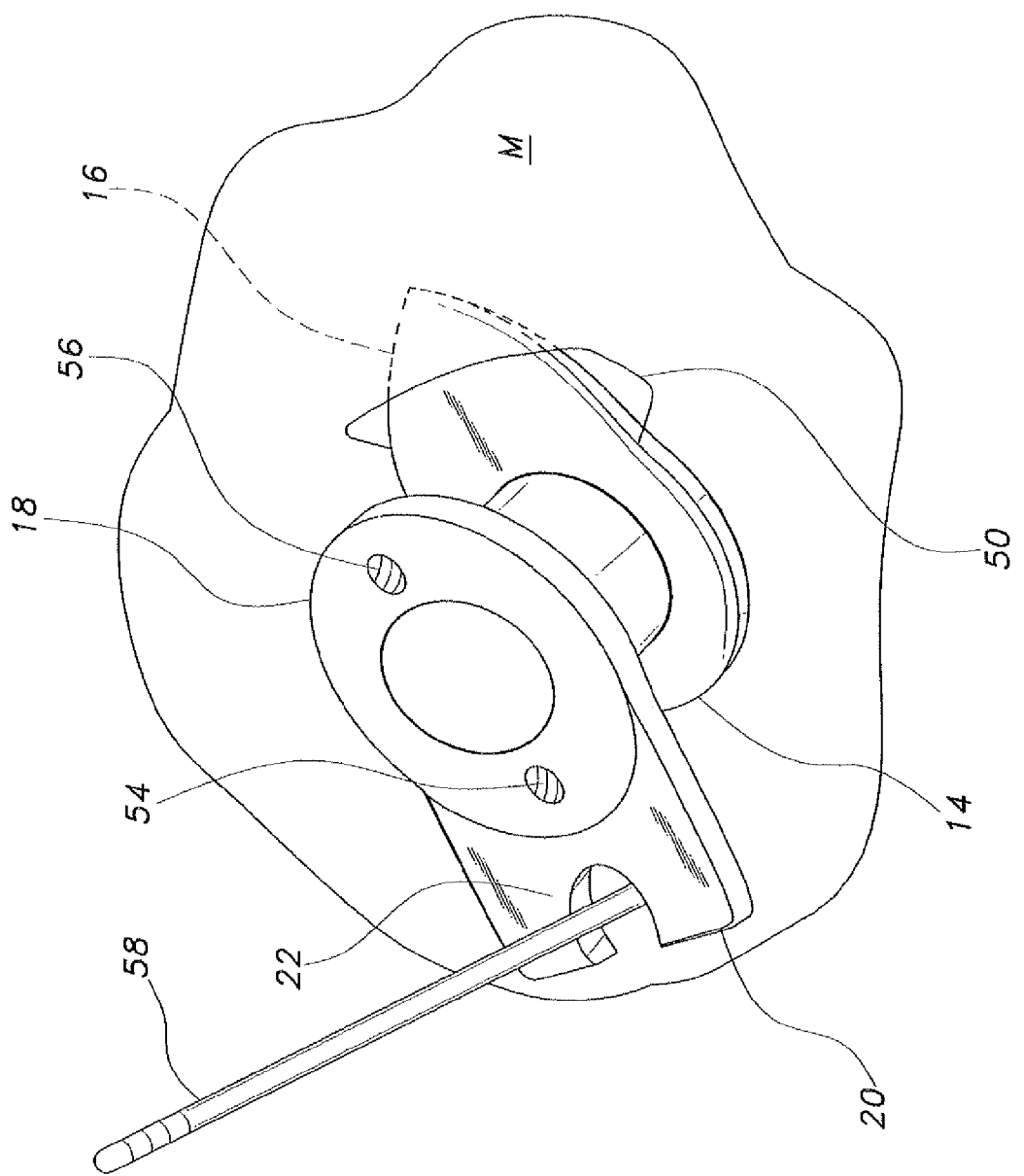
FIG. 5 is an environmental, perspective view of the middle ear ventilation tube of FIG. 2, illustrating insertion of the middle ear ventilation tube through a hole in the patient's tympanic membrane.
Figure 6:
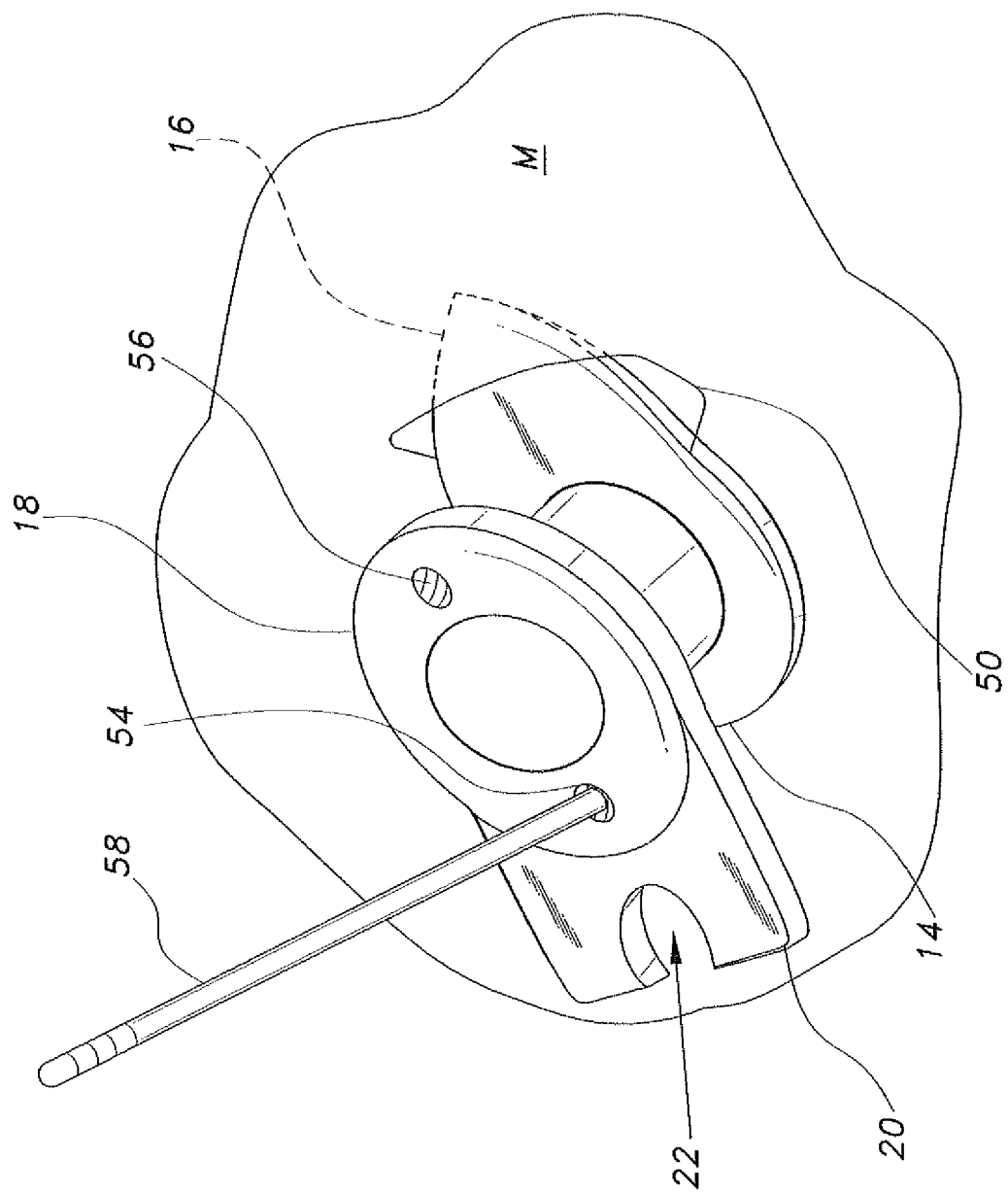
FIG. 6 is an environmental, perspective view of the middle ear ventilation tube of FIG. 2, illustrating fine adjustment of the position of the middle ear ventilation tube.

The tapered angled edge 16 of the first annular flange 14 is then inserted through a hole or opening 50 which has been conventionally incised, by a scalpel or the like, in the patient's tympanic membrane M. The tube 12 is next inserted through the opening 50 formed through the tympanic membrane M. As shown in FIG. 5, the notch 22 formed in the outer edge 24 of the tongue portion 20 is releasably engaged by a straight tip needle 58 or the tip of a similar instrument to properly position the first annular flange 14 adjacent the tympanic membrane M within the patient's middle ear ME, and to position the second annular flange 18 adjacent the tympanic membrane M within the patient's ear canal C on the opposite side of the tympanic membrane M. The first and second annular flanges 14, 18 maintain the tube 12 in place, ensuring that the tube does not slide through the opening 50 in either direction. As shown in FIG. 6, additional fine manipulation and positioning is effected by releasably engaging the pair of recesses 54, 56 with the tip of the straight tip needle 58.

The usage of the notch 22 for releasably engaging the needle 58, rather than continuous use of forceps 52, is because the needle 58 is thinner in profile than forceps 52, thus providing the surgeon with a better view within the ear, as the surgeon's line of sight would typically be blocked by the larger forceps 52. The needle 58 also allows for finer and more delicate adjustment than the bulkier forceps.

It is to be understood that the present invention is not limited to the embodiments described above, but encompasses any and all embodiments within the scope of the following claims.

I claim:

1. A middle ear ventilation tube, comprising:
 a hollow, substantially cylindrical tube having axially opposed first and second open ends;
 a first annular flange formed about the first end of the tube, the first annular flange defining first and second portions, the first portion defining an annular rim extending radially outward from the open first end of the tube, and the second portion defining a tapered angle edge; and
 a second annular flange formed about the second end of the tube, the second annular flange having a tongue portion extending outwardly therefrom and being diametrically opposed to the tapered angle edge, the tongue having an outer edge and a rounded, substantially C-shaped notch formed in the outer edge, wherein the second annular flange has a pair of recesses defined therein for fine adjustment of the position of the tube within the ear, wherein the pair of recesses are disposed solely on the second annular flange and are radially spaced apart from the second open end of the tube, the pair of recesses being diametrically opposed to one another with respect to the second open end of the tube.

2. The middle ear ventilation tube as recited in claim 1, wherein the tapered angled edge extends at an angle from the first portion.

3. The middle ear ventilation tube as recited in claim 1, wherein the tongue portion extends at an angle from said second annular flange.

4. The middle ear ventilation tube as recited in claim 1, wherein the tongue portion and the tapered angled edge extending substantially parallel to one another in diametrically opposite directions.

5. A method of ventilating a tympanic membrane, comprising the steps of:
 providing a middle ear ventilation tube having a hollow, substantially cylindrical tube having:
  a first annular flange formed about the first end of the tube, the first annular flange defining first and second portions, the first portion defining an annular rim extending radially outward from the open first end of the tube, and the second portion defining a tapered angle edge; and
  a second annular flange formed about the second end of the tube, the second annular flange having a tongue portion extending outwardly therefrom and being diametrically opposed to the tapered angle edge, the tongue having an outer edge and a rounded, substantially C-shaped notch formed in the outer edge, wherein the second annular flange has a pair of recesses defined therein for fine adjustment of the position of the tube within the ear, wherein the pair of recesses are disposed solely on the second annular flange and are radially spaced apart from the second open end of the tube, the pair of recesses being diametrically opposed to one another with respect to the second open end of the tube;
 inserting the middle ear ventilation tube into a patient's ear canal;
 inserting the tube through the opening formed through the tympanic membrane until the first annular flange lodges in the middle ear, the second annular flange remaining outside the middle ear;
 engaging the notch formed in the outer edge of the tongue portion with a straight tip needle; and
 positioning the first annular flange adjacent the tympanic membrane within the patient's middle ear, and the second annular flange adjacent the tympanic membrane within the patient's ear canal.

6. The method of ventilating a tympanic membrane as recited in claim 5, further comprising the step of engaging the pair of recesses with the straight tip needle to adjust the middle ear ventilation tube with respect to the tympanic membrane.

7. The method of ventilating a tympanic membrane as recited in claim 6, wherein the step of engaging the notch formed in the outer edge of the tongue portion with the straight tip needle comprises releasably engaging the notch with the straight tip needle.

* * * * *